(12) United States Patent
Strair

(10) Patent No.: US 8,575,216 B2
(45) Date of Patent: Nov. 5, 2013

(54) METHOD OF TREATMENT FOR ACUTE MYELOGENOUS LEUKEMIA

(75) Inventor: Roger Strair, Skillman, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 223 days.

(21) Appl. No.: 12/849,926

(22) Filed: Aug. 4, 2010

(65) Prior Publication Data

US 2011/0034425 A1    Feb. 10, 2011

Related U.S. Application Data

(60) Provisional application No. 61/273,446, filed on Aug. 4, 2009.

(51) Int. Cl.
*A01N 37/02* (2006.01)
*G01N 33/48* (2006.01)

(52) U.S. Cl.
USPC .......................................... 514/548; 436/63

(58) Field of Classification Search
None
See application file for complete search history.

(56) References Cited

FOREIGN PATENT DOCUMENTS

WO    WO 2008094657 A1 *    8/2008

OTHER PUBLICATIONS

Strair et al., Nuclear Factor-_B Modulation in Patients Undergoing Induction Chemotherapy for Acute Myelogenous Leukemia, Clinical Cancer Research (2008), 14(22), 7564-7568.*
Sato et al., Phorbol esters potentiate glucocorticoid-induced cytotoxicity in CEM-C7 human T-leukemia cell line (Abstract), Leuk Res. 1988;12(1):3-9.*
Han et al., Effect of intravenous infusions of 12-O-tetradecanoylphorbol-13-acetate (TPA) in patients with myelocytic leukemia: Preliminary studies on therapeutic efficacy and toxicity, *Proc. Natl. Acad. Sci.* vol. 95, pp. 5357-5361, Apr. 1998.
Fabre C. et al., NF-κB inhibition sensitizes to starvation-induced cell death in high-risk myelodysplastic syndrome and acute myeloid leukemia, *Oncogene* (2007) 26, 4071-4083.
Birkenkamp Ku et al., Constitutive NF-κB DNA-binding activity in AML is frequently mediated by a Ras/P13-K/PKB-dependent pathway, *Leukemia* (2004) 18, 103-112.
Frelin C. et al., Targeting NF-κB activation via pharmacologic inhibition of IKK2-induced apoptosis of human acute myeloid leukemia cells, *Blood* (2005) 105, 804-811.
Guzman Monica L. et al., Nuclear factor-κB is constitutively activated in primitive human acute myelogenous leukemia cells, *Blood* (2001) 98, 2301-2307.
Aghai, Zubair et al., Dexamethasone Suppresses Expression of Nuclear Factor-kappaB in cells of Tracheobronchial Lavage Fluid in Premature Neonates with Respiratory Distress, *Pediatric Research* (2006) vol. 59, No. 6, 811-815.
Schaar, Dale et al., A phase 1 clinical trial of 12-*O*-tetradecanoylphorbol-13-acetate for patients with relapsed/refractory malignancies, *Cancer Chemother Pharmacol* (2006) 57, 789-795.
Katerinaki, Efthymia et al., Sodium salicylate inhibits TNF-α-induced NF-κB activation, cell migration, invasion and ICAM-1 expression in human melanoma cells, *Melanoma Research* (2006) 16, 11-22.
Bueso-Ramos, Carlos E. et al., Expression of Constitutively Active Nuclear-κB ReIA Transcription Factor in Blasts of Acute Myeloid Leukemia, *Human Pathology* (Feb. 2004) vol. 35, No. 2, 246-253.
Klampfer, Lidija et al., Sodium Salicylate Activated Caspases and Induces Apoptosis of Myeloid Leukemia Cell Lines, *Blood* (Apr. 1, 1999), vol. 93, No. 7, 2386-2394.
Takada, Yasunari et al., Nonsteroidal anti-inflammatory agents differ in their ability to suppress NF-κB activation, inhibition of expression of cyclooxygenase-2 and cyclin D1, and abrogation of tumor cell proliferation, *Oncogene* (2004) 23, 9247-9258.
Yamamoto, Yumi et al., Sulindac Inhibits Activation of the NF-κB Pathway, *J. of Biological Chem.* (1999), vol. 274, No. 38, 27307-27314.

* cited by examiner

*Primary Examiner* — Sreeni Padmanabhan
*Assistant Examiner* — Svetlana M Ivanova
(74) *Attorney, Agent, or Firm* — Fox Rothschild LLP

(57) ABSTRACT

This invention relates to a method of treating acute myelogenous leukemia with TPA along with Dexamethasone and choline magnesium trisalicylate.

1 Claim, 6 Drawing Sheets

METHOD OF TREATMENT FOR ACUTE MYELOGENOUS LEUKEMIA

This application claims benefit of priority to U.S. Provisional Application Ser. No. 61/273,446, filed Aug. 4, 2009, the content of which is incorporated herein by reference in its entirety.

This invention relates to a method of treating acute myelogenous leukemia with TPA along with Dexamethasone and choline magnesium trisalicylate.

Acute Myelogenous Leukemia (AML) is an aggressive disease that generally warrants urgent and intensive therapy. The average patient age at AML diagnosis is 64-68 years old, and patients over the age of 60 treated with standard chemotherapy are cured of their disease<20% of the time. Patients who develop AML after an antecedent hematologic disorder or prior leukemogenic chemotherapy/radiation therapy have similarly poor outcomes, as do patients whose disease is associated with specific adverse cytogenetic and clinical features. Hence, most patients diagnosed with AML have patient and/or disease-related features that are associated with a very poor prognosis. For patients with relapsed disease, no standard non-transplant therapy has demonstrated the capacity for cure. For these patients, AML is often a fatal disease. New approaches to the therapy of AML are needed.

A new therapeutic approach to the treatment of AML has now been developed. More particularly, the method of the invention relates to the treatment of a patient diagnosed with AML with a combination of 12-O-tetradecanoylphorbol-13-acetate (TPA) in combination with dexamethasone and choline magnesium trisalicylate (CMT).

In one embodiment of the invention the TPA is administered at a fixed dose of 1 mg per week for 3 consecutive weeks. In addition dexamethasone and CMT are used as adjunctive medications because they are anti-inflammatory, may ameliorate adverse effects, and may enhance anti-leukemic activity by inhibition of the anti-apoptotic effects of: (i) constitutive NF-κB expression see below, and (ii) induction of phosphatases that decrease signaling pathway activity. CMT is chosen because it has been used in conjunction with dexamethasone in patients with leukemia and it does not inhibit platelet function.

12-O-tetradecanoylphorbol-13-acetate (TPA), an activator of protein kinase C, is being developed as a therapeutic agent for patients with acute myelogenous leukemia (AML) because of its profound effects on intracellular signaling pathways, it's capacity to induce differentiation and/or apoptosis in cell lines, and preliminary clinical data from China indicating effectiveness in myeloid malignancies (Han Z T, Zhu X X, Yang R Y, Sun J Z, Tian G F, Liu X J et al. Effect of intravenous infusions of 12-O-tetradecanoylphorbol-13-acetate (TPA) in patients with myelocytic leukemia: preliminary studies on therapeutic efficacy and toxicity. Proc Natl Acad Sci USA 1998; 95(9):5357-5361). A recently completed Investigator-initiated, Phase I study at The Cancer Institute of New Jersey/Robert Wood Johnson Medical School/UMDNJ represented the only FDA-approved study to administer TPA to patients in the United States and provided a unique opportunity to study the in vivo effects of TPA in patients with relapsed/refractory malignancies for which no standard therapies exist. Thus far clinical evaluation of TPA as a single agent has documented clinical safety when administered on days 1-5 and 8-12. However, responses comparable to that seen in China were not detected.

In a small panel of clinical AML samples, there is a subset of AML cases in which TPA has direct cytotoxic effects, as measured by cell viability and apoptosis assays. In all primary cultures analyzed by Western analysis, TPA strongly induced ERK phosphorylation by 1 hour in culture. However, TPA's cytotoxic effect on primary AML cells is associated with the subsequent loss of the phospho-ERK pro-survival signal after 24 hour ex vivo exposure. This observation is in good agreement with other studies that reported decreased primary AML survival after pharmacological interruption of ERK signaling by MEK inhibitors, such as PD98059, U0126 and PD 184352. In our studies, loss of ERK signaling was associated with induction of ERK phosphatases.

Figure 1:
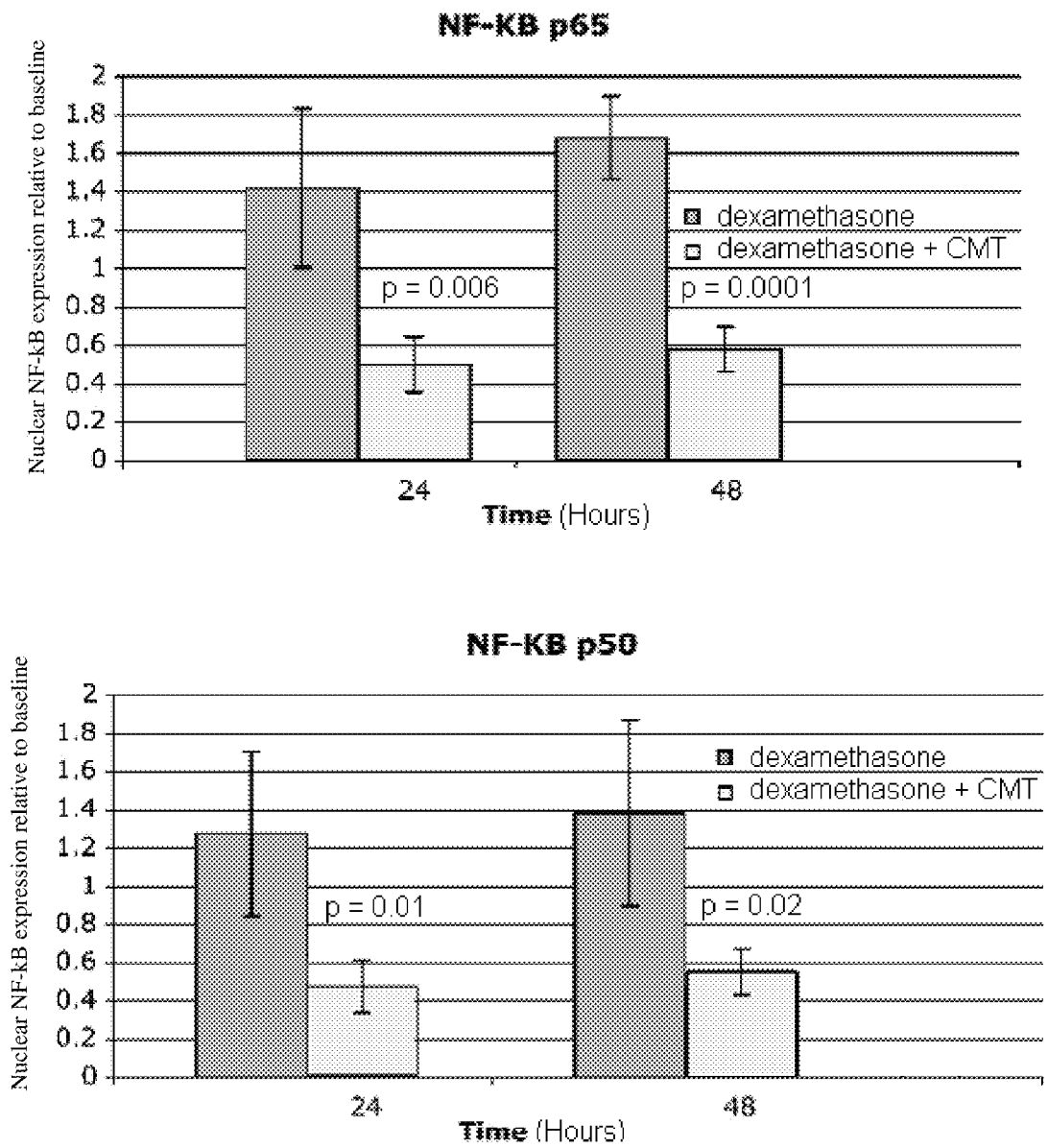
FIG. 1 shows nuclear NF-κB p50 and p65 response to treatment with dexamethasone and CMT.

In addition to protein kinase C and ERK activation, TPA is a known inducer of NF-κB, a pro-survival transcription factor often constitutively active in AML blasts and leukemic stem cells. In experimental models, suppression of NF-κB in leukemia cells is cytotoxic to AML cells (and leukemia stem cells). Recent work from our laboratory has demonstrated that AML cell NF-κB can be inhibited in vivo with 24-48 h of treatment with dexamethasone+CMT (see FIG. 1, wherein Mean ELISA of nuclear NF-κB p50 and p65 expression relative to baseline (time 0: pre-treatment)+/−SD 24 h after start of dexamethasone+/−CMT and 48 h after start of dexamethasone+/−CMT. Five patients received dexamethasone and five patients received dexamethasone+CMT. 24 h time point corresponds to the start of induction chemotherapy. The ordinate represents nuclear NF-κB expression relative to baseline.). In addition, dexamethasone can induce MKP-1 ERK phosphatase expression and enhance TPA cytotoxicity on primary AML samples. In this context, we have chosen to use dexamethasone and CMT as adjunctive medications to be used 24 h pre- and 24 h post treatment with TPA. These medications are well-tolerated, anticipated to reduce inflammatory adverse effects of treatment, and enhance TPA cytotoxicity by increasing ERK phosphatase expression and inhibiting NF-κB. CMT does not have clinically relevant anti-platelet effects and has minimal GI toxicity. The capacity of dexamethasone+choline magnesium trisalicylate to suppress nuclear NF-κB activity in AML in vivo in humans is demonstrated in FIG. 1 wherein mean ELISA of nuclear NF-κB p50 and p65 expression relative to baseline (time 0: pre-treatment)+/−SD 24 h after start of dexamethasone+/−CMT and 48 h after start of dexamethasone+/−CMT. Five patients received dexamethasone and five patients received dexamethasone+CMT. 24 h time point corresponds to the start of induction chemotherapy. The ordinate represents nuclear NF-κB expression relative to baseline. This study is more fully described below.

The initial CINJ TPA Phase 1 study enrolled 35 patients [23 with relapsed/refractory AML, 2 with other myeloid malignancies (CML-blast crisis, myelodysplasia with excess blasts), 3 with Hodgkin's Disease, 3 with non-Hodgkin's lymphoma and 4 with solid tumors]. The majority of patients had relapsed/refractory AML. Our clinical results include one AML patient with stable disease for >5 months, who received 8 TPA infusions. In a second AML patient, a pronounced (5-fold) decline in the number of circulating blasts was seen following TPA administration. This decline in leukemic blasts persisted for 4 weeks; the patient eventually died from a fungal infection. Finally, a patient with relapsed and refractory Hodgkin's disease despite high dose chemotherapy with autologous stem cell rescue had a partial remission of a chest wall mass after TPA administration. TPA dose escalation has been completed, in the last cohort 2 out of 3 patients treated at a dose of 0.188 mg/m² d1-5, 8-12 experienced grade III non-hematologic dose limiting toxicities (DLT), establishing the maximum tolerated TPA dose as a single agent at 0.125 mg/m²/d on d1-5 and 8-12.

Although ex vivo exposure of clinical AML samples with TPA concentrations as low as 0.032 nM results in detectable increases in ERK phosphorylation, the cytotoxic effects in general appear to be greater at higher TPA concentrations (e.g. 32 nM is more cytotoxic than 3.2 nM (unpublished observations). Cui et al have reported the use of a sensitive bioassay to measure TPA levels in our patient blood samples and detected on average 1.75 ng/ml blood [or 2.8 nanomolar (nM)] immediately post-infusion and a 0.93 ng/ml blood [or 1.5 nanomolar (nM)] average level one hour post infusion. These results were obtained from 5 patients infused at the maximum tolerated TPA dose of 0.125 mg/m². These observations suggest that further TPA dose escalation, may translate into better clinical responses, as seen in China. Hence we propose using a fixed dose of TPA 1 mg/week, as used in China.

Figure 2:
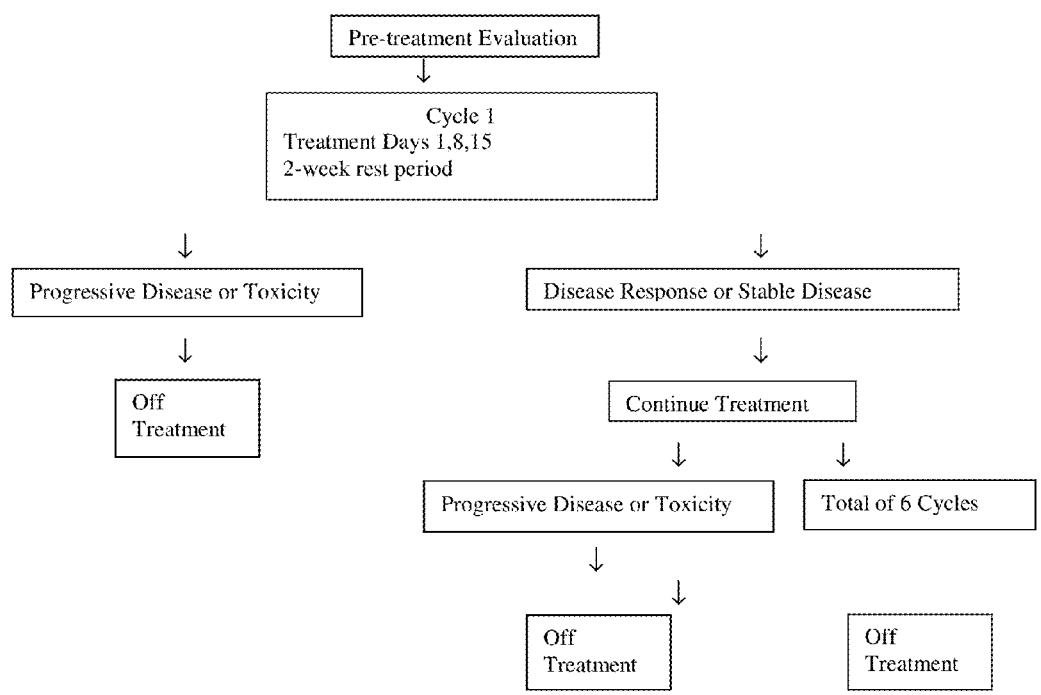
FIG. 2 shows one embodiment of a treatment path of the invention.

The DLT's reported from the CINJ TPA study were: grade 3 dyspnea, grade 3 hypoxia and a grade 3 episode of hypotension. Our clinical experience gained through the initial TPA protocol has indicated that many of the clinical side effects such as transient fever, dyspnea and phlebitis may be related to TPA-induced cytokine release and subsequent inflammatory processes. In a new study we will utilize a 1 mg dose of TPA as a fixed weekly dose for 3 consecutive weeks. We will also administer dexamethasone and CMT as anti-inflammatory agents anticipated to decrease adverse effects and increase TPA-cytotoxicity (by reducing ERK and NF-κB activation). One embodiment of a treatment plan is set forth in FIG. 2.

Advances in our understanding of acute myelogenous leukemia (AML) cell/molecular biology are guiding the development of new therapies. In AML, cellular proliferation, differentiation, and apoptosis are affected by complementing genetic alterations that deregulate signaling and transcription pathways. In addition, analysis of intrapatient cellular diversity with respect to proliferation, differentiation, and self renewal has identified a small subpopulation of cells that functions as leukemia stem cells. Therapeutic targeting of this population is essential for curing AML. One potential AML and LSC target is the transcription factor nuclear factor-κB (NF-κB) family. NF-κB transcription factors control the expression of various genes regulating inflammation, cell survival, and proliferation. In the classic NF-κB pathway, family members p65 (RelA) and p50 (NF-κB1) are localized in the cytoplasm of unstimulated cells as inactive dimers bound to inhibitors of NF-κB (IκB). Cell activation by cytokines, stress signals, and other stimuli results in IκB phosphorylation, leading to its degradation and subsequent nuclear accumulation of p50/p65 dimers which activate target gene transcription. Nuclear NF-κB is constitutively expressed in 47% to 100% of AMLs. In a study that addressed NF-κB activity in AML cells with the immunophenotype of LSCs, 11 of 11 isolated cell populations had constitutive nuclear expression that was not detected in normal hematopoietic stem cells. Ex vivo inhibition of NF-κB with a proteasome inhibitor alone, or in conjunction with an anthracycline or salicylate, induced apoptosis in AML cells and LSCs. Similarly, treatment of AML cells with an inhibitor of IκB phosphorylation resulted in NF-κB inhibition and apoptosis of leukemic cells but not normal hematopoietic stem cells.

Hence, NF-κB is an excellent target in AML. Given the dependence of AML cells and LSCs on NF-κB expression, we undertook a clinical trial to determine if we could achieve NF-κB modulation in conjunction with induction chemotherapy. We chose to study the commonly used anti-inflammatory agents dexamethasone and choline magnesium trisalicylate (CMT) because they inhibit NF-κB expression in a variety of cells, including AML cells, and are widely used inexpensive medications with well-characterized adverse effects. In addition, salicylate has been shown to induce apoptosis in AML cell lines and PC12 cells. Individually, they are sporadically used during AML therapy to treat fever, nausea, and allergic reactions. CMT exhibits fewer gastrointestinal effects than aspirin and doesn't have clinically significant effects on platelets. Hence, short-term use was felt likely to be well-tolerated in combination with standard AML chemotherapy. CMT was not studied alone initially because clinically achievable drug levels were not anticipated to inhibit NF-κB. However, testing of CMT alone was incorporated into the study after initial results showed the biochemical efficacy of the combination.

Our results indicate that NF-κB p50 and p65 inhibition in AML cells can be achieved with commonly used anti-inflammatory agents administered for a short time prior to, and immediately after, the initiation of induction chemotherapy. We chose to test dexamethasone and CMT because they are widely used, inexpensive, and could be administered at standard doses in conjunction with induction chemotherapy. We did not detect any unusual untoward effects attributable to dexamethasone or CMT. Too few patients were treated to assess the clinical efficacy of adding these agents to standard AML induction chemotherapy. In some clinical settings, NF-κB nuclear expression in cancer cells has been associated with a poor response to chemotherapy. In addition, agents such as anthracyclines could induce nuclear NF-κB, potentially leading to cellular antiapoptotic gene expression that attenuates cytotoxicity. Although doxorubicin-induced NF-κB may not induce the same pattern of gene regulation as constitutively expressed NF-κB, and may even be required for optimum cell kill in some systems, several studies show enhanced AML cytotoxicity ex vivo when chemotherapy is combined with the inhibition of NF-κB. Furthermore, inhibition of NF-κB is associated with loss of viability in LSCs. Hence, NF-κB inhibition should be formally tested in phase 2 trials of AML therapy designed to establish the toxicities and effects of NF-κB inhibition on target gene expression and clinical response. The availability of simple, inexpensive pharmacologic inhibition of NF-κB p50 and p65 during AML induction chemotherapy, as described in this report, will facilitate such testing.

EXPERIMENTAL

Clinical trial. A clinical trial was done to determine the temporal changes in leukemic cell NF-κB activity when anti-inflammatory agents dexamethasone F CMT were administered to patients with non-M3 AML for 48 h, beginning 24 h prior to induction chemotherapy. The study was an open-label trial. All patients provided informed consent approved by the Robert Wood Johnson Medical School Institutional Review Board. Patients>18 years old with non-M3 AML who had >5,000 leukemic blasts/mm3 were assigned to dexamethasone F CMT after providing informed consent approved by our Institutional Review Board. After the first 10 patients, the study was amended to treat an additional 4 patients with CMT alone. Inclusion criteria included non-pregnant patients with an Eastern Cooperative Oncology Group performance status of 0 to 3, a bilirubin level more than twice the upper limits of normal, aspartate aminotransferase/alanine aminotransferase level more than thrice the upper limits of normal, and creatinine levels more than 1.5 times the upper limits of normal. Patients with current or recent gastrointestinal bleeding were excluded. The clinical trial was investigator-initiated without industry support. Dexamethasone was administered at a dose of 10 mg p.o. every 6 h beginning at hour 0 and continuing until hour 48. CMT was administered at a dose of 1,500 mg every 8 h from hour 0 to hour 48. Induction chemotherapy consisted of 3 days of idarubicin in combination with a 7-day continuous infusion of cytarabine. Some patients over the age of 60 received a reduced dose of idarubicin and the addition of etoposide (32). Patient demographics are summarized in Table 1.

TABLE 1

Patient characteristics

| Patient no. | Age (sex) | Treatment | Diagnosis |
|---|---|---|---|
| 1 | 46 (M) | DEX | AML inv 16 |
| 2 | 62 (M) | DEX + CMT | AML t(3; 10) |
| 3 | 68 (F) | DEX | AML complex cytotoxicity |
| 4 | 57 (M) | DEX + CMT | AML inv 16 |
| 5 | 68 (F) | DEX | AML del(7) |
| 7 | 34 (M) | DEX + CMT | AML normal cytotoxicity |
| 8 | 65 (M) | DEX | AML normal cytotoxicity |
| 9 | 54 (F) | DEX + CMT | AML normal cytotoxicity |
| 10 | 49 (F) | DEX | AML trisomy 11 |
| 11 | 59 (M) | DEX +CMT | AML trisomy 8 |
| 12 | 58 (M) | CMT | AML normal cytotoxicity |
| 13 | 72 (F) | CMT | AML normal cytotoxicity |
| 14 | 65 (M) | CMT | AML normal cytotoxicity |
| 15 | 79 (M) | CMT | AML trisomy 11 |

Abbreviations:
M, male;
F, female;
DEX, dexamethasone

Measurement of NF-kB.

NF-κB levels at 0 (baseline), 24, and 48 h were determined by ELISA. Nuclear extracts from $1\times10^7$ cells isolated from 10 mL of fresh heparinized blood by istopaque centrifugation were prepared as described by others (33). The DNA binding activity in the nuclear extracts was quantified with the use of Trans AM NF-κB p50 and p65 ELISA kits (Active Motif), following the instructions of the manufacturer. Repeated measurement models were used to analyze the treatment and time effects on nuclear p50 and p65. The covariates included treatment, time, and the interaction between treatment and time. When the interaction was not significant, it was not included in the final model. Based on the final model, pairwise comparisons were also done. The Tukey method was used to adjust the multiplicity of the tests. A significance level of 5% (false-positive rate) was used for all the tests.

Results

Figure 3A:
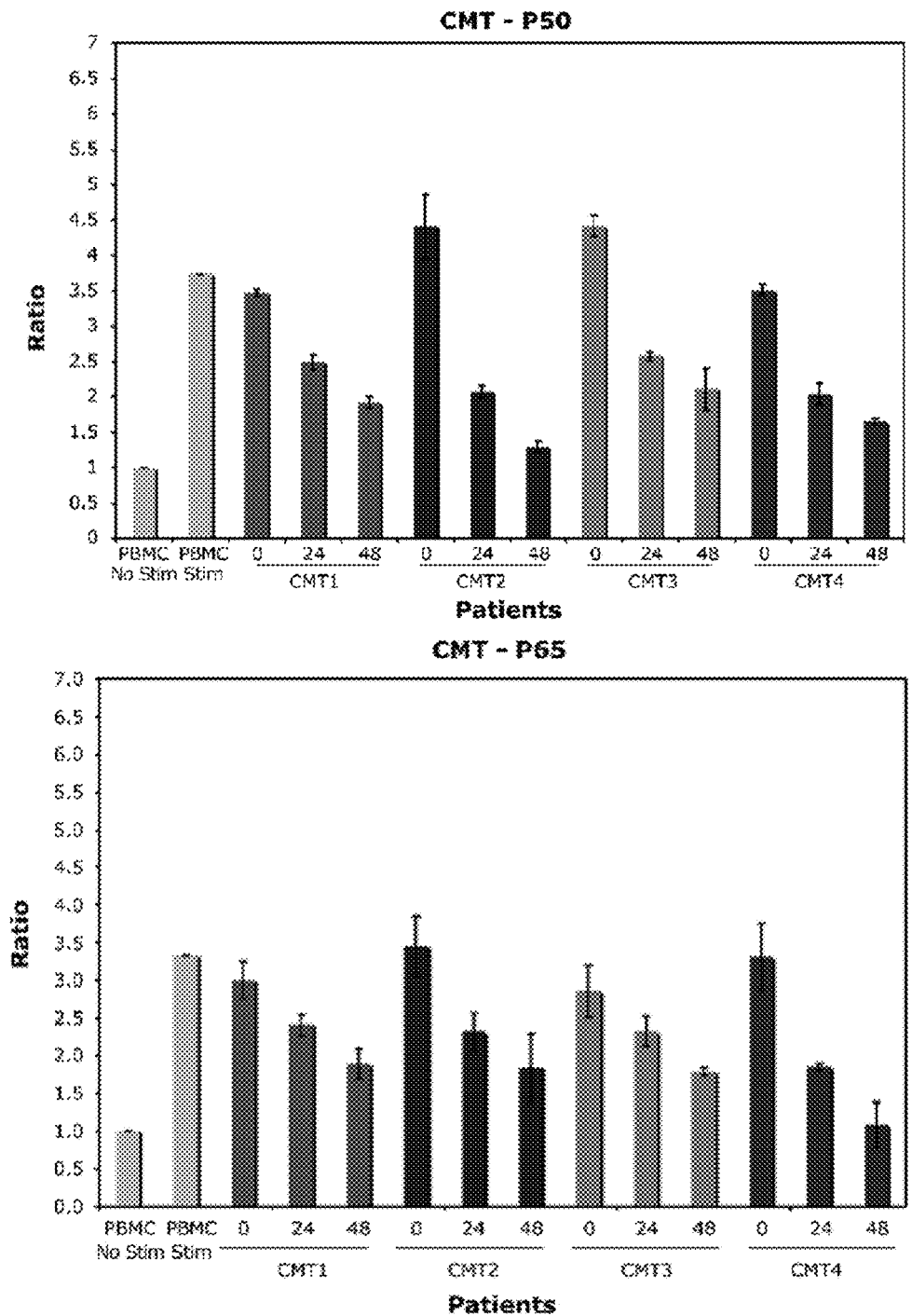
FIG. 3 shows nuclear NF-κB p50 and p65 response to treatment in individual patients.
Figure 3B:
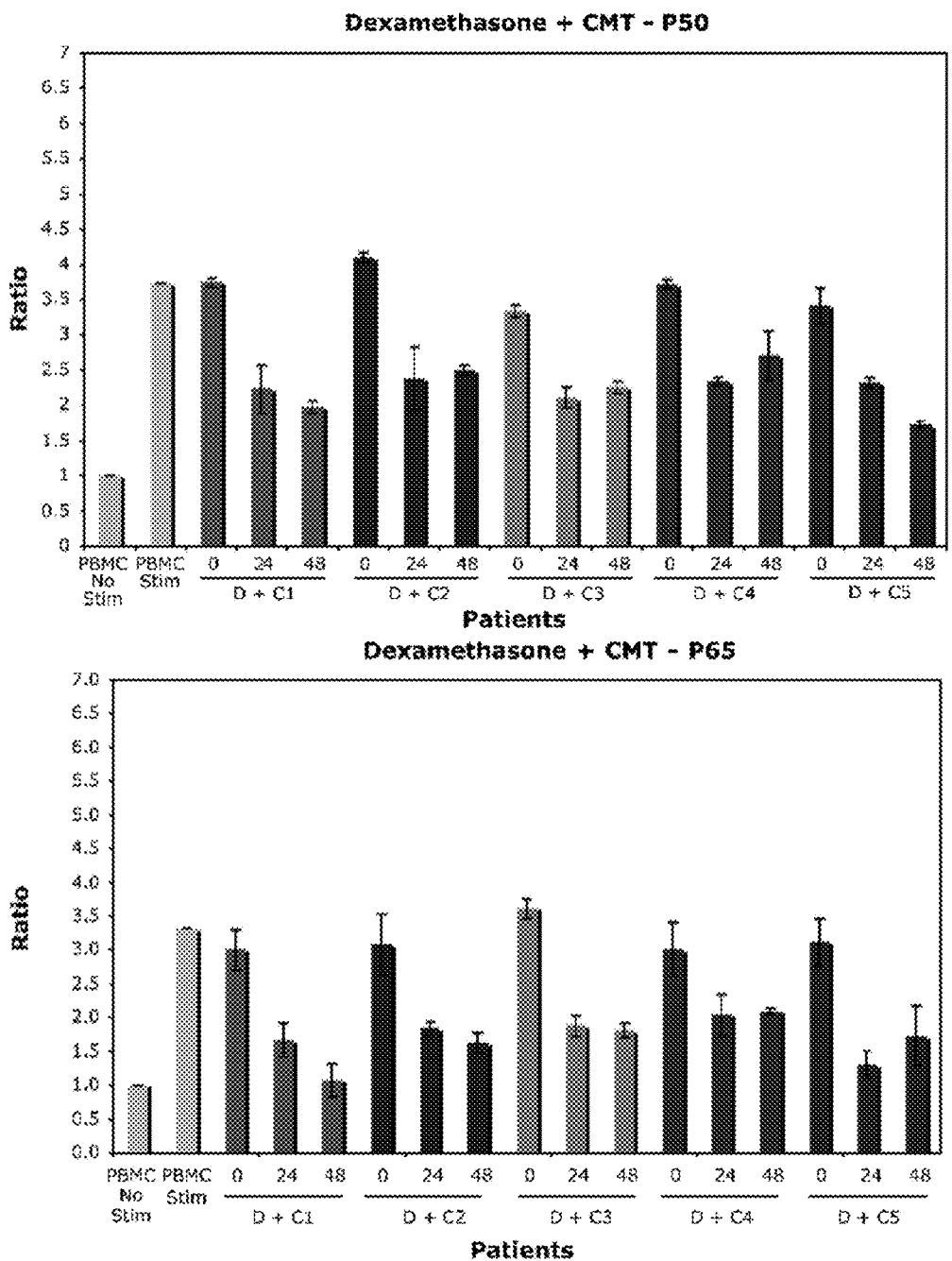
Figure 3C:
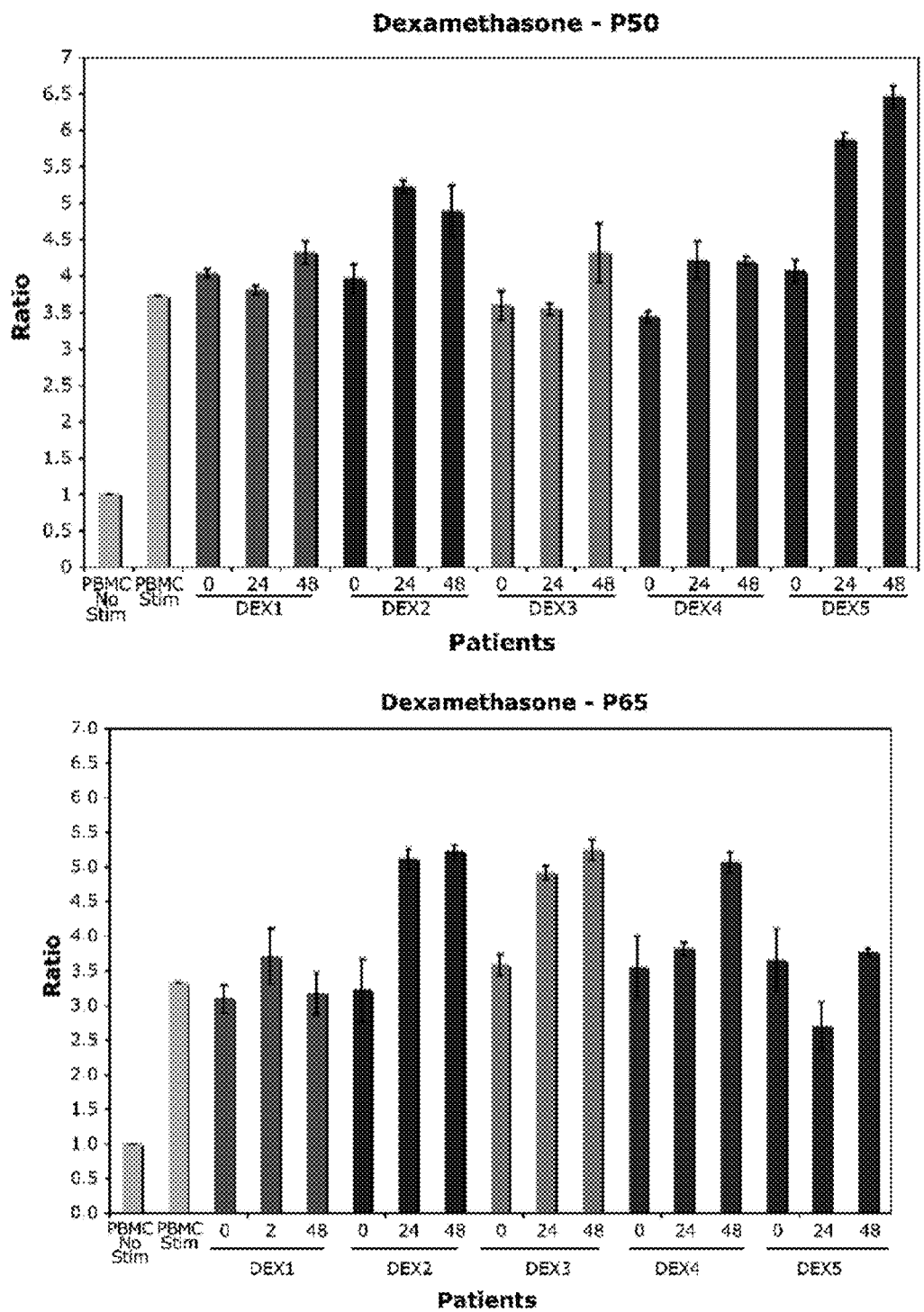
Figure 4:
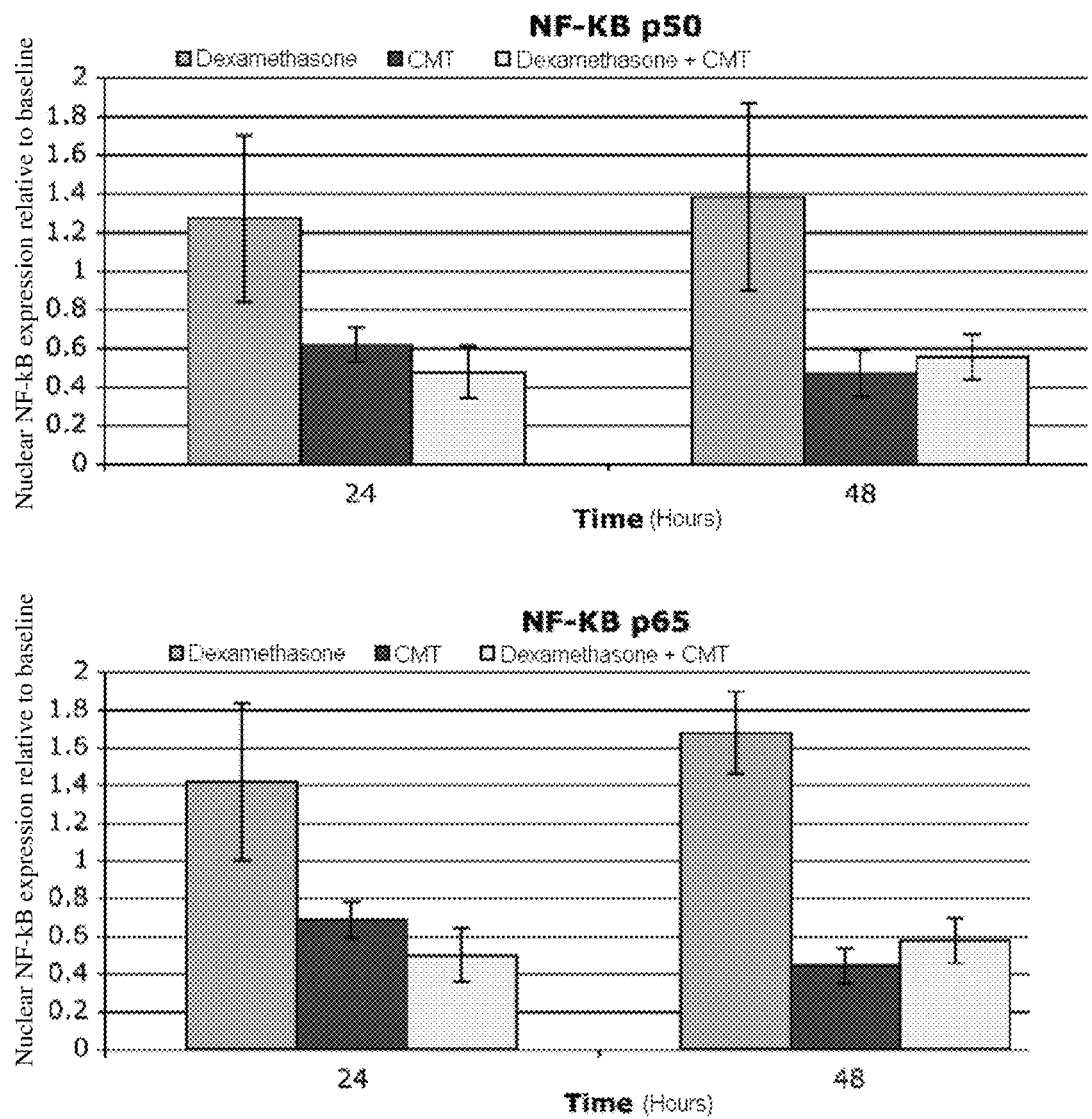
FIG. 4 shows nuclear NF-κB p50 and p65 response to treatment.

To develop NF-κB as a therapeutic target in AML, we did a pilot clinical trial to determine the feasibility of NF-κB inhibition by dexamethasone, CMT, or the combination for 48 hours (24 hours prior to and 24 hours following the initiation of induction chemotherapy). Fourteen patients were enrolled. Patient characteristics are presented in Table 1. Levels of nuclear p50 and p65 were increased in comparison to unstimulated blood mononuclear cells (obtained from a volunteer donor) in all samples (FIG. 3). There was no relationship between presenting WBC count and levels of nuclear p50 or p65. All nine patients receiving dexamethasone+CMT or CMT had reductions below baseline of both p50 and p65 at 24 hours (prior to initiation of induction chemotherapy) and 48 hours (24 hours after initiation of induction chemotherapy). Levels of nuclear p50 decreased by 27% to 48% at 24 hours and 35% to 71% at 48 hours, and levels of nuclear p65 decreased by 20% to 41% at 24 hours and 47% to 69% at 48 hours in comparison to baseline in patients treated with CMT (FIG. 3A). Levels of nuclear p50 decreased by 37% to 71% at 24 hours and 27% to 57% at 48 hours, and levels of nuclear p65 decreased by 32% to 67% at 24 hours and 30% to 58% at 48 hours in comparison to baseline values in patients treated with dexamethasone+CMT (FIG. 3B). In contrast, nuclear levels of p50 ranged from a decrease by 20% to an increase of 70% at 24 hours and no change to an increase of 80% compared with baseline at 48 hours in patients treated with dexamethasone alone. Similarly, nuclear levels of p65 ranged from unchanged to a 110% increase at 24 hours and a 20% to 80% increase at 48 hours in patients treated with dexamethasone alone 7). No patients receiving dexamethasone alone had reductions of p50 and p65 below the baseline at 48 hours (24 hours after the initiation of chemotherapy). Statistical analysis revealed these treatment group differences for p50 and p65 levels at 24 and 48 hours to be highly significant when comparing dexamethasone alone to dexamethasone+CMT or CMT alone (P<0.001), and was not significant when comparing dexamethasone+CM to CMT (P z 0.9700; FIG. 4, where columns, mean ELISA of nuclear NF-κB p50 and p65 relative to baseline; bars: SD (time 0, pretreatment); 24 h after start of dexamethasone, CMI, or both; and 48 h after start of treatment. The 24-h time point represents nuclear NF-κB levels prior to initiation of chemotherapy. Five patients received dexamethasone alone, five patients received dexamethasone CMT, and four patients received CMT alone. The ordinate represents nuclear expression relative to baseline (time 0).). These results show the in vivo inhibition of nuclear NF-κB p50 and p65 in AML cells by CMT F dexamethasone administered for a short time prior to, and immediately after, the initiation of induction chemotherapy. We did not, detect any unusual untoward elects attributable to dexamethasone or CMT, either alone or in combination.

1. Han Z T, Zhu X X, Yang R Y, Sun J Z, Tian G F, Liu X J et al. Effect of intravenous infusions of 12-O-tetradecanoylphorbol-13-acetate (TPA) in patients with myelocytic leukemia: preliminary studies on therapeutic efficacy and toxicity. Proc Natl Acad Sci U S A 1998; 95(9):5357-5361.
2. Schaar D, Goodell L, Aisner J, Cui X X, Han Z T, Chang R et al. A phase I clinical trial of 12-O-tetradecanoylphorbol-13-acetate for patients with relapsed/refractory malignancies. Cancer Chemother Pharmacol 2006; 57(6):789-795.
3. Schaar D G, Liu H, Sharma S, Ting Y, Martin J, Krier C et al. 12-O-tetradecanoylphorbol-13-acetate (TPA)-induced dual-specificity phosphatase expression and AML cell survival. Leuk Res 2005; 29(10):1171-1179.
4. Cui X X, Chang R L, Zheng X, Woodward D, Strair R, Conney A H. A sensitive bioassay for measuring blood levels of 12-O-tetradecanoylphorbol-13-acetate (TPA) in patients: preliminary pharmacokinetic studies. Oncol Res 2002; 13(3):169-174.
5. Milella M, Kornblau S M, Estrov Z, Carter B Z, Lapillonne H, Harris D et al. Therapeutic targeting of the MEK/MAPK signal transduction module in acute myeloid leukemia. J Clin Invest 2001; 108(6):851-859.
6. Morgan M A, Dolp O, Reuter C W. Cell-cycle-dependent activation of mitogen-activated protein kinase kinase (MEK-1/2) in myeloid leukemia cell lines and induction of growth inhibition and apoptosis by inhibitors of RAS signaling. Blood 2001; 97(6):1823-1834.

7. Birkenkamp K U, Geugien M, Schepers H, Westra J, Lemmink H H, Vellenga E. Constitutive NF-kappaB DNA-binding activity in AML is frequently mediated by a Ras/PI3-K/PKB-dependent pathway. Leukemia 2004; 18(1):103-112.
8. Braun T, Carvalho G, Coquelle A, Vozenin M C, Lepelley P, Hirsch F et al. NF-kappaB constitutes a potential therapeutic target in high-risk myelodysplastic syndrome. Blood 2006; 107(3):1156-1165.
9. Fabre C, Carvalho G, Tasdemir E, Braun T, Ades L, Grosjean J et al. NF-kappaB inhibition sensitizes to starvation-induced cell death in high-risk myelodysplastic syndrome and acute myeloid leukemia. Oncogene 2007.
10. Frelin C, Imbert V, Griessinger E, Peyron A C, Rochet N, Philip P et al. Targeting NF-kappaB activation via pharmacologic inhibition of IKK2-induced apoptosis of human acute myeloid leukemia cells. Blood 2005; 105(2):804-811.
11. Guzman M L, Neering S J, Upchurch D, Grimes B, Howard D S, Rizzieri D A et al. Nuclear factor-kappaB is constitutively activated in primitive human acute myelogenous leukemia cells. Blood 2001; 98(8):2301-2307.
12. Guzman M L, Rossi R M, Karnischky L, Li X, Peterson D R, Howard D S et al. The sesquiterpene lactone parthenolide induces apoptosis of human acute myelogenous leukemia stem and progenitor cells. Blood 2005; 105(11):4163-4169.
13. Adcock I M. Glucocorticoids: new mechanisms and future agents. Curr Allergy Asthma Rep 2003; 3(3):249-257.
14. Adcock I M, Ito K, Barnes P J. Glucocorticoids: effects on gene transcription. Proc Am Thorac Soc 2004; 1(3):247-254.
15. Aghai Z H, Kumar S, Farhath S, Kumar M A, Saslow J, Nakhla T et al. Dexamethasone suppresses expression of Nuclear Factor-kappaB in the cells of tracheobronchial lavage fluid in premature neonates with respiratory distress. Pediatr Res 2006; 59(6):811-815.
16. Kagoshima M, Ito K, Cosio B, Adcock I M. Glucocorticoid suppression of nuclear factor-kappa B: a role for histone modifications. Biochem Soc Trans 2003; 31(Pt 1):60-65.
17. Katerinaki E, Haycock J W, Lalla R, Carlson K E, Yang Y, Hill R P et al. Sodium salicylate inhibits TNF-alpha-induced NF-kappaB activation, cell migration, invasion and ICAM-1 expression in human melanoma cells. Melanoma Res 2006; 16(1):11-22.
18. Kiss K, Kiss J, Rudolf E, Cervinka M, Szeberenyi J. Sodium salicylate inhibits NF-kappaB and induces apoptosis in PC12 cells. J Biochem Biophys Methods 2004; 61(1-2):229-240.
19. Klampfer L, Cammenga J, Wisniewski H G, Nimer S D. Sodium salicylate activates caspases and induces apoptosis of myeloid leukemia cell lines. Blood 1999; 93(7):2386-2394.
20. Takada Y, Bhardwaj A, Potdar P, Aggarwal B B. Nonsteroidal anti-inflammatory agents differ in their ability to suppress NF-kappaB activation, inhibition of expression of cyclooxygenase-2 and cyclin D1, and abrogation of tumor cell proliferation. Oncogene 2004; 23(57):9247-9258.
21. Palombella V J, Rando O J, Goldberg A L, Maniatis T. The ubiquitin-proteasome pathway is required for processing the NF-kappa B1 precursor protein and the activation of NF-kappa B. Cell 1994; 78(5):773-785.
22. Dash A, Gilliland D G. Molecular genetics of acute myeloid leukaemia. Best Pract Res Clin Haematol 2001; 14:49-64.
23. Bonnet D, Dick J E. Human acute myeloid leukemia is organized as a hierarchy that originates from a primitive hematopoietic cell. Nat Med 1997; 3:730-7.
24. Bonnet D. Normal and leukemic stem cells. BrJHaematol 2005; 130:469-79.
25. Xiao G, Rabson A B, Young W, Qing G, Qu Z. Alternative pathways of NF-κB activation: a double-edged sword in health and disease. Cytokine Growth Factor Rev 2006; 17:281-93.
26. Braun T, Carvalho G, Fabre C, Grosjean J, Fenaux P, Kroemer G. Targeting NF-κB in hematologic malignancies. Cell Death Differ 2006; 13:748-58.
27. Bueso-Ramos C E, Rocha F C, Shishodia S, et al. Expression of constitutively active nuclear-κBRelAtranscription factor in blasts of acute myeloid leukemia. Hum Pathol 2004; 35:246-53.
28. Guzman M L, Swiderski C F, Howard D S, et al. Preferential induction of apoptosis for primary human leukemic cells. ProcNatlAcadSciUSA 2002; 99:16220-5.
29. Guzman M L, Rossi R M, Karnischky L, et al. The sesquiterpene lactone parthenolide induces apoptosis of Cancer Therapy: Clinical Clin Cancer Res 2008; 14(22) Nov. 15, 2008 7568 www.aacrjournals.org human acute myelogenous leukemia stem and progenitor cells. Blood 2005; 105:4163-9.
30. Yamamoto Y, Yin M-J, Lin K-M, Gaynor R B. Sulindac inhibits activation of the NF-κB pathway. J Biol Chem 1999; 274:27307.
31. Yamamoto Y, Gaynor R B. Therapeutic potential of inhibition of NF-κB pathway in the treatment of inflammation and cancer. JClin Invest 2001; 107:135.
32. Leoni F, Ciolli S, Giuliani G, et al. Attenuated-dose idarubicin in acute myeloid leukaemia of the elderly: pharmacokinetic study and clinical results. Br J Haematol 1995; 90:169-74.
33. Andrews N C, Faller D V. A rapid micropreparation technique for extraction from DNA-binding proteins from limiting numbers of mammalian cells. Nucleic Acids Res 1991; 19:2499.
34. Lindsey J K. Models for repeated measurements. Oxford: Clarendon Press; 1993.
35. Buchholz A K, Garg T A, Chakravarti N, et al. The nuclear transcription factor κB/bcl-2 pathway correlates with pathologic complete response to doxorubicin-based neo-adjuvant chemotherapy in human breast cancer. Clin Cancer Res 2005; 11:8398-402.
36. How W C, Dickson K M, Barker P A. Nuclear factor-κB induced by doxorubicin is deficient in phosphorylation and acetylation and represses nuclear factor-κBdependent transcription in cancer cells. Cancer Res 2005; 65:427381.
37. Ashikawa K, Shishodia S, Fokt I, Priebe W, Aggarwal B B. Evidence that activation of nuclear factor-κB is essential for the cytotoxic effects of doxorubicin and its analogues. Biochem Pharmacol 2004; 67:353-64.

The invention claimed is:
1. A method of treating a patient suffering from acute myelogenous leukemia which comprises administering to the patient an effective amount of 12-O-tetradecanoylphorbol-13-acetate (TPA) along with dexamethasone and choline magnesium trisalicylate.

* * * * *